US006348464B1

(12) United States Patent
Jackson et al.

(10) Patent No.: US 6,348,464 B1
(45) Date of Patent: Feb. 19, 2002

(54) PYRROLECARBONYLIMINO DERIVATIVES AS NAALADASE INHIBITORS

(75) Inventors: Paul F. Jackson, Bel Air; Barbara S. Slusher, Kingsville, both of MD (US)

(73) Assignee: Guilford Pharmaceuticals, Inc., Baltimore, MD (US)

( * ) Notice: Subject to any disclaimer, the term of this patent is extended or adjusted under 35 U.S.C. 154(b) by 0 days.

(21) Appl. No.: 09/438,970

(22) Filed: Nov. 12, 1999

(51) Int. Cl.$^7$ ........................ A61K 31/53; A61K 31/40; A61K 31/415; A61K 31/495; A61K 31/17
(52) U.S. Cl. ........................ 514/241; 514/422; 514/423; 514/385; 514/388; 514/396; 514/401; 514/402; 514/255; 514/256; 514/260; 514/272; 514/588; 514/595; 514/597; 514/249; 514/252
(58) Field of Search ........................ 514/422, 423, 514/385, 388, 396, 401, 402, 403, 255, 256, 260, 272, 588, 595, 597, 241, 252, 249

(56) References Cited

U.S. PATENT DOCUMENTS

| | | |
|---|---|---|
| 4,950,738 A | 8/1990 | King et al. |
| 5,242,915 A | 9/1993 | Ueda et al. |
| 5,262,568 A | 11/1993 | Weber et al. |
| 5,336,689 A | 8/1994 | Weber et al. |
| 5,474,547 A | 12/1995 | Aebischer et al. |
| 5,500,420 A | 3/1996 | Maiese |
| 5,804,602 A | 8/1998 | Slusher et al. |
| 5,824,662 A | 10/1998 | Slusher et al. |
| 5,863,536 A | 1/1999 | Jackson et al. |
| 5,880,112 A | 3/1999 | Jackson et al. |
| 5,902,817 A | 5/1999 | Jackson et al. |
| 5,977,090 A | 11/1999 | Slusher et al. |
| 6,017,903 A | 1/2000 | Slusher et al. |

FOREIGN PATENT DOCUMENTS

| | | |
|---|---|---|
| WO | 93/21942 | 11/1993 |
| WO | WO 95/23806 | 9/1995 |
| WO | WO 97/28796 | 8/1997 |
| WO | 98/45256 | 10/1998 |

OTHER PUBLICATIONS

Stauch, et al., "The Effects of N–Acetylated Alpha–Linked Acidic Dipeptidase (NAALADase) Inhibitors on [$^3$H] NAAG Catabolism In Vivo", *Neuroscience Letters*, (1989) 100:295–300.

Subasinghe, N. et al., "Synthesis of Acyclic and Dehydroaspartic Acid Analogues of Ac–Asp–Glu–OH and Their Inhibition of Rat Brain N–Acetylated α–linked Acidic Dipeptidase (NAALA Dipeptidase)", *J. Med. Chem.*, (1990) 33: 2734–2744.

Slusher, B. et al., "Rat Brain N–Acetylated α–Linked Acidic Dipeptidase Activity", *J. Biological Chemistry*, (1990) 265: 21297–301.

Rothstein, J. et al., "Abnormal Excitatory Amino Acid Metabolism in Amyotrophic Lateral Sclerosis", *Annals of Neurology*, (1990) 28 :18–25.

Tsai, G. et al., "Reductions in Acidic Amino Acids and N–Acetylaspartylglutamate in Amyotrophic Lateral Sclerosis CNS", *Brain Research*, (1991) 556: 151–156.

Coyle, J. et al., "N–Acetyl–aspartyl Glutamate", *Excitatory Amino Acids*, (1991) 69–77.

Slusher, B. et al., "Immunocytochemical Localization of the N–Acetyl–Aspartyl–Glutamate (NAAG) Hydrolyzing Enzyme N–Acetylated α–Linked Acidic Diepetidase (NAALADase)", *J. of Comp. Neurology*, (1992) 315: 217–229.

Myerhoff, J. et al., "Activity of NAAG–Hydrolyzing Enzyme in Brain May Affect Seizure Susceptibility in Genetically Epilepsy–Prone Rats", *Molecular Neurobiology of Epilepsy (Epilepsy Res.*, Suppl. 9), (1992) 163–172.

Myerhoff, J. et al., "Genetically Epilepsy–Prone Rats Have Increased Brain Regional Activity of an Enzyme Which Liberates Glutamate from N–Acetyl–Aspartyl–Glutamate", *Brain Research*, (1992) 593: 140–43.

Tsai et al., 61$^{st}$ Salmon Lecturer of the New York Academy of Medicine, Dec. 2–3, 1993, "Changes of Excitatory Neurotransmitter Metabolism in Schizophrenic Brains", *Brain Research*, (1991) 556: 151–156.

Slusher et al., "NAALADase: a Potential Regulator of Synaptic Glutamate.", *Biotech Update Dupont NEN*, (1994) 9:37–39.

Koenig, M. et al., "N–Acetyl–Asparyl–Glutamate (NAAG) Elicits Rapid Increase in Intraneuronal $Ca^{2+}$ In Vitro", *NeuroReports*, (1994) 5: 1063–1068.

Vornov, J.et al., "Toxic NMDA–Receptor Activation Occurs During Recovery in a Tissue Culture Model of Ischemia", *J. of Neurochemistry*, (1995) 65:1681–91.

Jackson, P. et al., "Design, Synthesis, and Biological Activity of a Potent Inhibitor of the Neuropeptidase N–Acetylated–Linked Acidic Dipeptidase", *J. of Medicinal Chemistry*, (1996) 39:619–622.

Woods, D., Hurn, P., et al., "Gender–Linked Injury after Focal Cerebral Ischemia", *Soc. for Neuroscience 1996 Abstract Form*, (1996).

Bhardwaj, Anish, et al., "Striatal Nitric Oxide (NO) Production Is Enhanced in Focal Cerebral Ischemia: an In Vivo Microdialysis Study,", *Society for Neuroscience 1996 Abstract Form*, (1996).

*Primary Examiner*—Theodore J. Criares
(74) *Attorney, Agent, or Firm*—Lyon & Lyon LLP

(57) ABSTRACT

The present invention relates to pharmaceutical compositions and methods of using pyrrolecarbonylimino derivatives to inhibit N-Acetylated α-Linked Acidic Dipeptidase (NAALADase) enzyme activity, thereby effecting neuronal activities, inhibiting angiogenesis, and treating glutamate abnormalities, compulsive disorders, prostate diseases and cancers.

23 Claims, 1 Drawing Sheet

FIG. 1A Suramin sodium
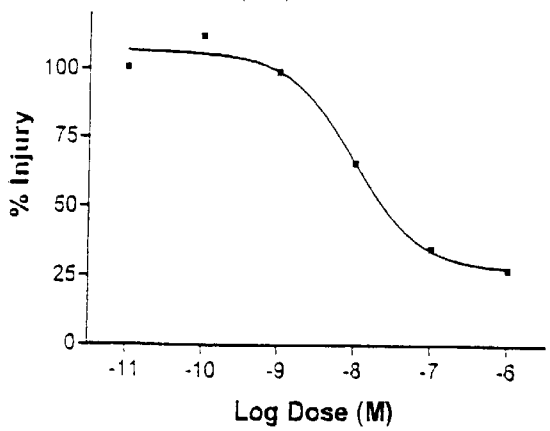
FIG. 1B 8-(3-nitrobenzamido)-1,3,5-naphthalenetrisulfonic acid
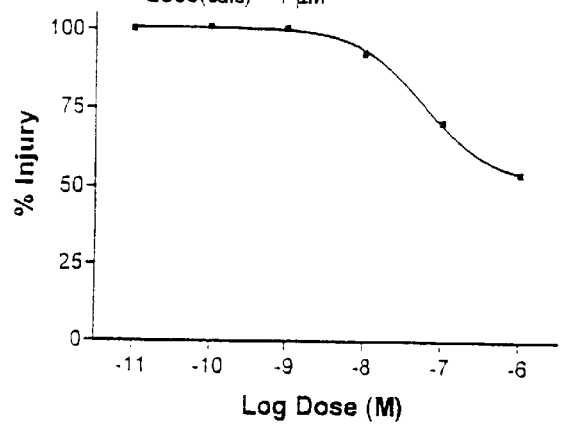
FIG. 1C 8,8'-[carbonylbis(imino-3,1-phenylene)]bis-(1,3,5-naphthalenetrisulfonic acid), sodium salt
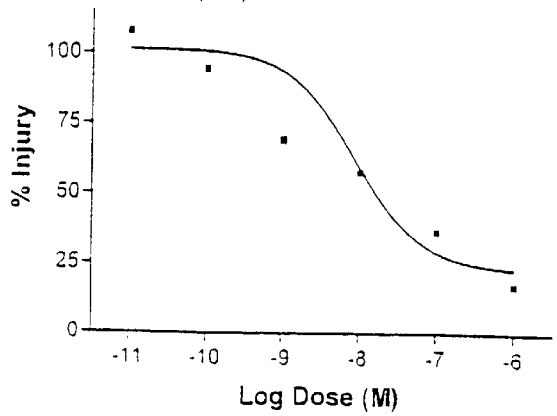

PYRROLECARBONYLIMINO DERIVATIVES AS NAALADASE INHIBITORS

BACKGROUND OF THE INVENTION

The present invention relates to pharmaceutical compositions and methods for effecting neuronal activities, inhibiting angiogenesis and treating glutamate abnormalities, compulsive disorders, prostate diseases and cancers using pyrrolecarbonylimino derivatives as N-acetylated α-linked Acidic Dipeptidase (NAALADase) enzyme inhibitors.

The NAALADase enzyme, also known as prostate specific membrane antigen (PSM or PSMA) and human glutamate carboxypeptidase II (GCP II), catalyzes the hydrolysis of the neuropeptide N-acetyl-aspartyl-glutamate ("NAAG") to N-acetyl-aspartate ("NAA") and glutamate. Based upon amino acid sequence homology, NAALADase has been assigned to the M28 family of peptidases. There is, as yet, no crystallographic evidence of the structure of the NAALADase enzyme.

Recent studies have implicated NAALADase in the pathogenesis of glutamate-mediated disorders. Neuropathological studies on post-mortem tissue from patients with amyotrophic lateral sclerosis (ALS) indicate large decreases of N-acetylaspartate (NAA) and N-acetylaspartylglutamate (NAAG) tissue concentrations occurring in association with neuronal degeneration, and increases of NAA and NAAG in cerebral spinal fluid (CSF) from patients with ALS. Concordantly, abnormal NAAG levels and NAALADase activity have also been observed in post-mortem prefrontal and limbic brain tissue of schizophrenic patients. Autopsy studies also suggest a strong correlation between NAAG/NAA and Alzheimer's disease. In post-mortem brain tissue, NAA and NAAG levels were found to be selectively decreased in brain areas (hippocampus and amygdala) affected by Alzheimer's disease pathology.

Glutamate serves as the predominant excitatory neurotransmitter in the central nervous system (CNS). Neurons release glutamate in greater quantities when they are deprived of oxygen, as may occur during an ischemic brain insult such as a stroke or a heart attack. This excess release of glutamate in turn causes over-stimulation (excitotoxicity) of N-methyl-D-aspartate (NMDA), AMPA, Kainate, MGR and MGluR receptors. When glutamate binds to these receptors, ion channels in the receptors open, permitting flows of ions across their cell membranes, e.g., $Ca^{2+}$ and $Na^+$ into the cells and $K^+$ out of the cells. These flows of ions, especially the influx of $Ca^{2+}$, cause over-stimulation of the neurons. The over-stimulated neurons secrete more glutamate, creating a feedback amplification effect which is believed to ultimately result in cell death via the production of proteases, lipases, and free radicals.

Excessive activation of glutamate receptors has been implicated in various neurological diseases and conditions (for example, spinal cord injury, epilepsy, stroke, Alzheimer's disease, Parkinson's Disease, Amyotrophic Lateral Sclerosis (ALS), Huntington's Disease, schizophrenia, acute and chronic pain, ischemia and neuronal loss following hypoxia, hypoglycemia, ischemia, trauma, nervous insult, compulsive disorders (particularly drug and alcohol dependence), demyelinating diseases, peripheral neuropathies, and diabetic neuropathy), as well as in the generation of long-term potentiation, which is regarded as an electrophysiological manifestation of learning and memory. Specifically, the NMDA subtype of glutamate receptor appears to be involved in learning processes because the NMDA antagonist 2-amino-5-phosphonopentanoate (AP5) selectively impairs learning and blocks long-term potentiation in rats. It has thus been proposed that deterioration in glutamatergic systems accounts for impairment in cognitive function observed in aged animals or in Alzheimer's disease.

In particular, glutamatergic abnormalities have been associated with schizophrenia. For example, phencyclidine (PCP) and other antagonists of N-methyl-D-aspartate (NMDA) receptors induce psychotomimetic properties in healthy individuals and exacerbate preexisting symptoms of schizophrenia, suggesting that a depression of glutamate transmission contributes to schizophrenia. Additionally, it has been reported that antagonists of non-NMDA receptors or pretreatments that attenuate glutamate release reduce mnemonic and other behavioral effects of NMDA receptor antagonists. Studies have also shown that stimulation of certain subtypes of mGlu receptors mediates presynaptic depression and decreases evoke release of glutamate.

Recent studies have also advanced a glutamatergic basis for compulsive disorders, particularly drug dependence. For example, neurophysiological and pathological effects of ethanol have been found to be mediated through the glutamatergic system. Specifically, acute exposure to ethanol disrupts glutamatergic neurotransmission by inhibiting ion flow through channels in glutamate receptors, whereas chronic exposure up-regulates the number of glutamate receptors and thereby increases ion flow. Acute withdrawal from ethanol results in hyperexcitability and seizures in the presence of up-regulated channels, thereby making postsynaptic neurons vulnerable to excitotoxic damage.

Post mortem examinations of histologically normal brains from alcoholics have shown that chronic alcoholism moderately increases the density of the NMDA subtype of glutamate receptors in the frontal cortex. This up-regulation may represent a stage of ethanol-induced chronic neurotoxicity. As such, neurobiological effects of alcoholism, including intoxication, withdrawal seizures, delirium tremens, Wernicke-Korsakoff syndrome and fetal alcohol syndrome, can be understood as a spectrum of the consequences of ethanol's effect on the glutamatergic system. In this regard, alcoholism may be considered another member of the expanding family of glutamate-related neurological disorders.

The glutamatergic system has also been implicated in the behavioral effects of other abused drugs. For example, studies have shown that glutamatergic antagonists block motor-stimulating activities induced by amphetamine and cocaine, and glutamatergic agonists cause the same stereotypy as that produced by amphetamine. These results represent pharmacological evidence that the expression of the stereotypic effect of psychomotor stimulants involves the glutamatergic system.

Epidemiologic studies have revealed a strong correlation between drug dependence and other compulsive disorders. Additionally, a common genetic anomaly has been found among people with alcoholism, cocaine dependence, nicotine dependence, pathological gambling, attention deficit disorder (ADD), Tourette's syndrome, compulsive overeating and obesity. Such disorders are believed to be manifestations of the effects of excitotoxicity.

Ischemic injury may occur as a focal or global disruption of blood supply. Following ischemic insult, widespread neuronal depolarization occurs. Depolarization stimulates release of the stored neurotransmitter glutamate and results in impaired capacity of glutamate uptake mechanisms. Impaired glutamate uptake and enhanced glutamate release contribute to sustained elevation of extracellular glutamate in ischemic tissue, and may result in tissue damage. As more damage occurs, more glutamate may be released. Although not limited to any particular theory, it is believed that by interfering with or eliminating this cascade of glutamate toxicity, the compositions and methods of the present convention may be clinically useful in curbing the progression of ischemic injury.

Afferent pain fibers of the A-δ and C types have their primary cell bodies in the dorsal root ganglia; central extensions of these nerve cells project, via the dorsal root, to the dorsal horn of the spinal cord or to the nucleus of the trigeminal nerve; the peripheral terminations of these primary pain receptors are the branch nerve endings in the skin and other organs. Excitatory amino acids, including glutamate, and ATP are putative neurotransmitters at the dorsal horn terminus of primary A-δ fibers. The conscious awareness or perception of pain occurs only when the pain impulses actually reach the thalamocortical level. Although not limited to any particular theory, it is believed that by interfering with such nerve impulses, the compositions and methods of the present invention will be clinically useful in limiting or eliminating pain.

Diabetic neuropathy is a slowly progressive, mixed sensorimotor and autonomic neuropathy. A variety of pathogenic mechanisms have been proposed for diabetic neuropathy, including alteration in nerve metabolism induced by ischemia and, in some cases, autoimmunity. Although not limited to any particular theory, it is believed that by interfering with or eliminating these effects, the compositions and methods of the present convention may be clinically useful in curbing the progression of diabetic neuropathy.

Excessive activation of glutamate receptors has been implicated in anxiety and anxiety disorders. Significantly higher glutamate plasma levels have been detected in patients with mood disorders than in comparison subjects. Studies also suggest that the pharmacological effect of anxiolytic agents is mediated through the glutamatergic system. Although not limited to any particular theory, it is believed that by interfering with or eliminating these effects, the compositions and methods of the present convention are expected to be clinically useful in curbing anxiolytic activity.

Based on the above findings, the present inventors tested and found NAALADase inhibitors to be efficacious in the pharmacotherapy of glutamate abnormalities, such as drug dependence, diabetic neuropathy, pain, schizophrenia, ischemic injury, and anxiety.

Most research and development activity to date has focused on blocking post-synaptic glutamate receptors with compounds such as NMDA antagonists, glycine antagonists, and other post-synaptic excitatory amino acid (EAA) receptor blockers. Unfortunately, these efforts have proven difficult because each receptor has multiple sites to which glutamate may bind; in addition, these agents produce severe toxicities even under normal conditions, thus limiting their clinical use. Although not limited to any one particular theory, it is believed that NAALADase inhibitors block glutamate release pre-synaptically without interacting with post-synaptic glutamate receptors. Since NAALADase inhibitors do not appear to alter basal glutamate levels, they may be devoid of the behavioral toxicities associated with post-synaptic glutamate antagonists.

In addition to glutamate, NAALADase has also been associated with prostate-specific membrane antigen (PSMA). In particular, it has been shown that PSMA cDNA confers NAALADase activity and that NAALADase and PSMA exhibit at least 86% homologous sequence identity. Carter et al., *Proc. Natl. Acad. Sci.*, Vol. 93, pp. 749–753 (1996). The molecular cloning of PSMA has been reported as a potential prostate carcinoma marker and hypothesized to serve as a target for imaging and cytotoxic treatment modalities for prostate cancer. Additionally, PSMA antibodies, particularly indium-111 labelled and itrium labelled PSMA antibodies, have been described and examined clinically for the diagnosis and treatment of prostate cancer. PSMA is expressed in prostatic ductal epithelium and is present in seminal plasma, prostatic fluid and urine.

Applicants have found NAALADase inhibitors to be effective in treating prostate diseases, particularly prostate cancer. Although not limited to any particular theory, it is believed that NAALADase inhibitors inhibit PSMA activity. Since mAbs to PSMA have been found to target 23 non-prostate carcinomas (Lui et al., *Science Research*, Vol. 57, pp. 3629–34 (1997)), the present inventors hypothesize that NAALADase inhibitors would also be effective in treating non-prostate cancers, particularly in tissues where NAALADase resides, such as the brain, kidney and testis.

NAALADase has also been found in neovasculature (new blood vessels). The present inventors have discovered that NAALADase inhibitors inhibit or prevent growth of neovasculature (angiogenesis), thereby providing potential therapeutic applications in treating diseases dependent upon angiogenesis. Examples of angiogenesis-dependent diseases include without limitation rheumatoid arthritis, cardiovascular disease, neovascular diseases of the eye, peripheral vascular disorders, and dermatologic ulcers. Angiogenesis is also essential for normal physiological processes, such as growth, fertility and soft tissue wound healing.

Cancer is another disease dependent upon angiogenesis. Cancer tumor cells secrete or release angiogenic substances that activate nearby endothelial cells. These endothelial cells respond by expressing a cell autonomous pattern of behavior that culminates in the formation of new blood vessels. Since research has demonstrated that angiogenesis is necessary to sustain the growth, invasion and metastasis of cancer tumors, the neovasculature inhibiting activity of NAALADase inhibitors further supports their utility in treating all types of cancers.

In view of the broad range of potential applications, a need exists for new NAALADase inhibitors, pharmaceutical compositions comprising such inhibitors, and methods of their use.

SUMMARY OF THE INVENTION

The present invention relates to pharmaceutical compositions and methods of using pyrrolecarbonylimino derivatives to inhibit N-Acetylated α-Linked Acidic Dipeptidase (NAALADase) enzyme activity, thereby effecting neuronal activities, inhibiting angiogenesis, and treating glutamate abnormalities, compulsive disorders, prostate diseases and cancers.

Specifically, the present invention relates to a method for inhibiting NAALADase enzyme activity in a mammal, comprising administering to said mammal an effective amount of a compound of formula I

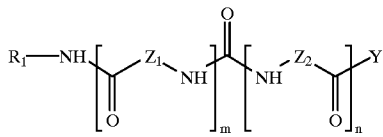

or a pharmaceutically acceptable equivalent, wherein:
m and n are independently 0, 1, 2 or 3;
Y is —$R_2$ or —$NHR_2$;
$R_1$ and $R_2$ are independently an aryl or heteroaryl group substituted with one or more substituent(s);
$Z_1$ and $Z_2$ are independently a moiety of formula II, III or IV

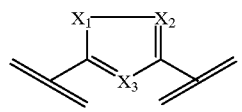

II

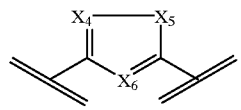

III

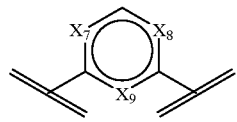

IV $X_1$ and $X_5$ are independently $CHR_3$ or $NR_3$;
$X_2$, $X_3$, $X_4$, $X_6$, $X_7$, $X_8$ and $X_9$ are independently $CR_3$ or N; and
$R_3$ is H or $CH_3$.

The present invention further relates to a method for treating a glutamate abnormality in a mammal, comprising administering to said mammal an effective amount of a compound of formula I

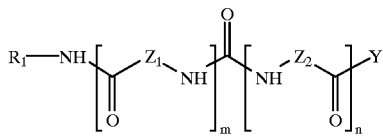

or a pharmaceutically acceptable equivalent, wherein:
m and n are independently 0, 1, 2 or 3;
Y is —$R_2$ or —$NHR_2$;
$R_1$ and $R_2$ are independently an aryl or heteroaryl group substituted with one or more substituent(s);
$Z_1$ and $Z_2$ are independently a moiety of formula II, III or IV

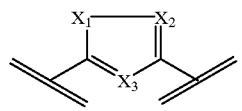

II

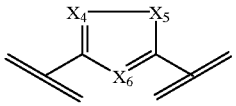

III

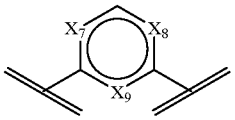

IV $X_1$ and $X_5$ are independently $CHR_3$ or $NR_3$;
$X_2$, $X_3$, $X_4$, $X_6$, $X_7$, $X_8$ and $X_9$ are independently $CR_3$ or N; and
$R_3$ is H or $CH_3$;
provided that when m and n are independently 1, 2 or 3, Y is —$NHR_2$, $R_2$ is naphthyl substituted with 1, 2 or 3 sulfonic acid(s), $Z_1$ and $Z_2$ are each a moiety of formula II, $X_1$ and $X_2$ are each CH, $X_3$ is $NR_3$, and $R_3$ is $CH_3$, then the glutamate abnormality is not a demyelinating disease; and when the compound of formula I is suramin, then the glutamate abnormality is not a CNS neurodegenerative disorder or a demyelinating disease.

The present invention further relates to a method for effecting a neuronal activity in a mammal, comprising administering to said mammal an effective amount of a compound of formula I

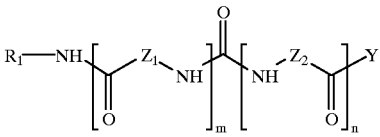

a pharmaceutically acceptable equivalent, wherein:
m and n are independently 0, 1, 2 or 3;
Y is —$R_2$ or —$NHR_2$;
$R_1$ and $R_2$ are independently an aryl or heteroaryl group substituted with one or more substituent(s);
$Z_1$ and $Z_2$ are independently a moiety of formula II, III or IV

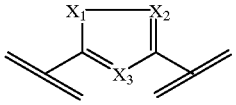

II

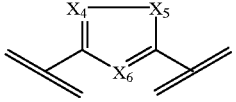

III

IV $X_1$ and $X_5$ are independently $CHR_3$ or $NR_3$;
$X_2$, $X_3$, $X_4$, $X_6$, $X_7$, $X_8$ and $X_9$ are independently $CR_3$ or N; and $R_3$ is H or $CH_3$;

provided that when m and n are independently 1, 2 or 3, Y is —$NHR_2$, $R_2$ is naphthyl substituted with 1, 2 or 3 sulfonic acid(s), $Z_1$ and $Z_2$ are each a moiety of formula II, $X_1$ and $X_2$ are each CH, $X_3$ is $NR_3$, and $R_3$ is $CH_3$, then the effecting a neuronal activity is not treating a demyelinating disease; and when the compound of formula I is suramin, then the effecting a neuronal activity is not treating a CNS neurodegenerative disorder or a demyelinating disease.

The present invention further relates to a method for treating a prostate disease in a mammal, comprising administering to said mammal an effective amount of a compound of formula I

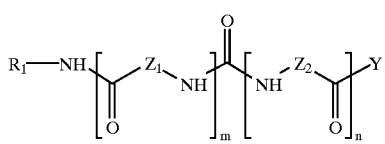

I or a pharmaceutically acceptable equivalent, wherein:

m and n are independently 0, 1, 2 or 3;

Y is —$R_2$ or —$NHR_2$;

$R_1$ and $R_2$ are independently an aryl or heteroaryl group substituted with one or more substituent(s);

$Z_1$ and $Z_2$ are independently a moiety of formula II, III or IV

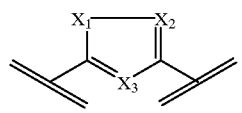

II

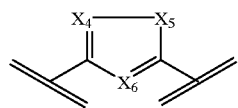

III

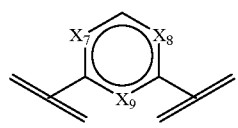

IV $X_1$ and $X_5$ are independently $CHR_3$ or $NR_3$;

$X_2$, $X_3$, $X_4$, $X_6$, $X_7$, $X_8$ and $X_9$ are independently $CR_3$ or N; and $R_3$ is H or $CH_3$;

provided that when the compound of formula I is suramin, then the prostate disease is not prostate cancer.

The present invention further relates to a method for treating cancer in a mammal, comprising administering to said mammal an effective amount of a compound of formula I

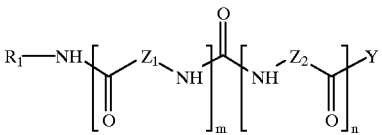

I or a pharmaceutically acceptable equivalent, wherein:

m and n are independently 0, 1, 2 or 3;

Y is —$R_2$ or —$NHR_2$;

$R_1$ and $R_2$ are independently an aryl or heteroaryl group substituted with one or more substituent(s);

$Z_1$ and $Z_2$ are independently a moiety of formula II, III or IV

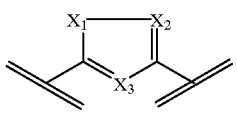

II

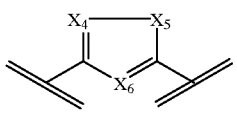

III

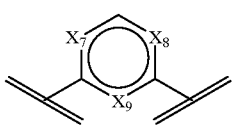

IV $X_1$ and $X_5$ are independently $CHR_3$ or $NR_3$;

$X_2$, $X_3$, $X_4$, $X_6$, $X_7$, $X_8$ and $X_9$ are independently $CR_3$ or N; and $R_3$ is H or $CH_3$;

provided that when the compound of formula I is suramin, then the cancer is not prostate cancer.

The present invention further relates to a method for inhibiting angiogenesis in a mammal comprising administering to said mammal an effective amount of a compound of formula I

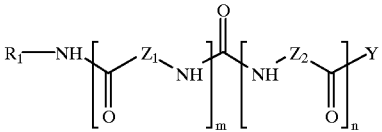

I or a pharmaceutically acceptable equivalent, wherein:

m and n are independently 0, 1, 2 or 3;

Y is —$R_2$ or —$NHR_2$;

$R_1$ and $R_2$ are independently an aryl or heteroaryl group substituted with one or more substituent(s);

$Z_1$ and $Z_2$ are independently a moiety of formula II, III or IV

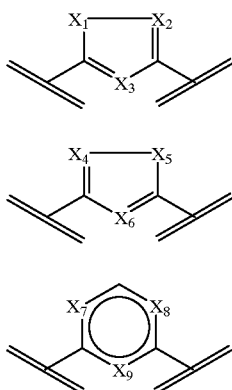

$X_1$ and $X_5$ are independently $CHR_3$ or $NR_3$;
$X_2$, $X_3$, $X_4$, $X_6$, $X_7$, $X_8$ and $X_9$ are independently $CR_3$ or N; and $R_3$ is H or $CH_3$.

The present invention further relates to a pharmaceutical composition comprising:
(i) an effective amount of a compound of formula I for inhibiting NAALADase enzyme activity or angiogenesis, effecting a neuronal activity, or treating a glutamate abnormality, prostate disease or cancer

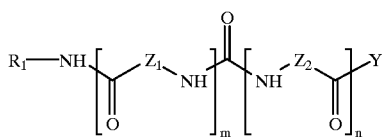

or a pharmaceutically acceptable equivalent, wherein:
m and n are independently 0, 1, 2 or 3;
Y is —$R_2$ or —$NHR_2$;
$R_1$ and $R_2$ are independently an aryl or heteroaryl group substituted with one or more substituent(s);
$Z_1$ and $Z_2$ are independently a moiety of formula II, III or IV

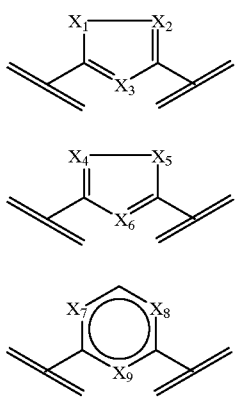

$X_1$ and $X_5$ are independently $CHR_3$ or $NR_3$;
$X_2$, $X_3$, $X_4$, $X_6$, $X_7$, $X_8$ and $X_9$ are independently $CR_3$ or N; and
$R_3$ is H or $CH_3$;
provided that when m and n are independently 1, 2 or 3, Y is —$NHR_2$, $Z_1$ and $Z_2$ are each a moiety of formula II, $X_1$ and $X_2$ are each CH, $X_3$ is $NR_3$, and $R_3$ is $CH_3$, then $R_2$ is not naphthyl substituted with 1, 2 or 3 sulfonic acid(s); and provided that the compound of formula I is not suramin; and
(ii) a pharmaceutically acceptable carrier.

INCORPORATION BY REFERENCE

In addition to other references generally known in the art, applicants have previously disclosed data relating to the relationship between glutamate and various glutamate abnormalities, and the effectiveness of NAALADase inhibitors generally with regard to treating ischemic insult, diminished neurological function, alcohol dependence, nicotine dependence, cancer cell and tumor growth, angiogenesis, cocaine dependence, diabetes, pain, and hyperalgesia. Applicants hereby incorporate by reference, as though set forth herein in full, such figures and discussions from U.S. Pat. Nos. 5,672,592, 5,795,877, 5,863,536, 5,880,112 and 5,902,817, allowed U.S. patent applications Ser. Nos. 08/825,997, 08/833,628, 08/842,360 and 08/899,319 for which the issue fees have been paid, and International Publications Nos. WO 97/48399, WO 97/48400, WO 97/48409 and WO 98/53812. It would be expected that the compounds of the present invention would be effective as NAALADase inhibitors, and as such would have the same uses as the aforementioned compounds.

The compounds of the present invention are available from commercial suppliers or can be readily prepared by an ordinarily skilled artisan using standard techniques such as those disclosed in U.S. Pat. No. 5,859,046, herein incorporated by reference, as though set forth herein in full.

BRIEF DESCRIPTION OF THE DRAWINGS

FIG. 1A is a graph plotting the effectiveness of Suramin sodium in protecting cortical cell cultures from the damaging effects of 2-deoxyglucose and potassium cyanide ischemic insult in vitro.

FIG. 1B is a graph plotting the effectiveness of 8-(3-nitrobenzamido)-1,3,5-naphthalenetrisulfonic acid in protecting cortical cell cultures from the damaging effects of 2-deoxyglucose and potassium cyanide ischemic insult in vitro.

FIG. 1C is a graph plotting the effectiveness of 8,8'-[carbonylbis(imino-3,1-phenylene)]bis-(1,3,5-naphthalenetrisulfonic acid) sodium salt in protecting cortical cell cultures from the damaging effects of 2-deoxyglucose and potassium cyanide ischemic insult in vitro.

DETAILED DESCRIPTION OF THE INVENTION

DEFINITIONS

"Attached" refers to bonding, linkage, coupling, or other molecular association between atoms or molecules which results in a stable chemical entity.

"Derivative" refers to a substance produced from another substance either directly or by modification or partial substitution.

"Effective amount" refers to the amount required to produce the desired effect. "Therapeutically effective amount" refers to the amount required to inhibit NAALADase enzyme activity, effect neuronal activity, inhibit angiogenesis, and/or treat glutamate abnormality, prostate disease and/or cancer.

"Electromagnetic radiation" includes without limitation radiation having the wavelength of $10^{-20}$ to $10^0$ meters. Preferred embodiments of the present invention employ the electromagnetic radiation of gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

"Half molecule" refers to the product of a division of a molecule of formula I along an axis of symmetry. For example, the compound 8,8'-[carbonylbis(imino-3,1-phenylene)]bis-(1,3,5-naphthalenetrisulfonic acid), 1,3,8-naphthalenetrisulfonic acid

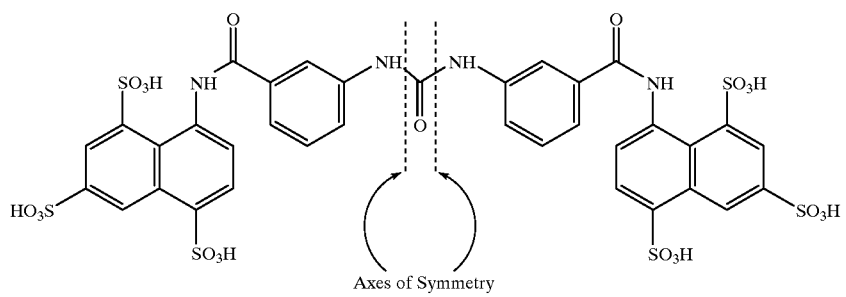

Axes of Symmetry may be divided along an axis of symmetry, and reduced to form the half molecule 8-(3-nitrobenzamido)-1,3,5-naphthalenetrisulfonic acid

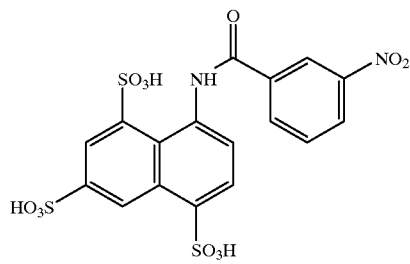

or a pharmaceutically acceptable equivalent.

"Isosteres" refer to elements, molecules, or ions having different molecular formulae but exhibiting similar or identical physical properties. For example, tetrazole is an isostere of carboxylic acid because it mimics the properties of carboxylic acid even though they both have very different molecular formulae. Typically, two isosteric molecules have similar or identical volumes and shapes. Ideally, isosteric compounds should be isomorphic and able to co-crystallize. Among the other physical properties that isosteric compounds usually share are boiling point, density, viscosity and thermal conductivity. However, certain properties are usually different: dipolar moments, polarity, polarization, size and shape since the external orbitals may be hybridized differently. The term "isosteres" encompass "bioisosteres".

"Bioisosteres" are isosteres which, in addition to their physical similarities, share some common biological properties. Typically, bioisosteres interact with the same recognition site or produce broadly similar biological effects.

"Carboxylic acid isosteres" include without limitation direct derivatives such as hydroxamic acids, acylcyanamides and acylsulfonamides; planar acidic heterocycles such as tetrazoles, mercaptoazoles, sulfinylazoles, sulfonylazoles, isoxazoles, isothiazoles, hydroxythiadiazoles and hydroxychromes; and nonplanar sulfur- or phosphorus-derived acidic functions such as phosphinates, phosphonates, phosphonamides, sulphonates, sulphonamides, and acylsulphonamides.

"Metabolite" refers to a substance produced by metabolism or by a metabolic process.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate. In addition, NAAG is an agonist at group II metabotropic glutamate receptors, specifically mGluR3 receptors; when attached to a moiety capable of inhibiting NAALADase, it is expected that metabotropic glutamate receptor ligands will provide potent and specific NAALADase inhibitors.

"NAALADase" refers to N-acetylated α-linked acidic dipeptidase, a membrane bound metallopeptidase which catabolizes NAAG to N-acetylaspartate ("NAA") and glutamate ("GLU"):

Catabolism of NAAG By NAALADase

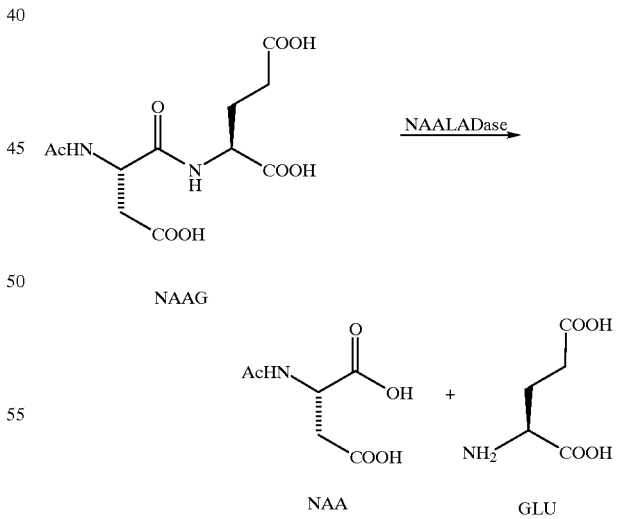

NAALADase has recently been assigned to the M28 peptidase family and is also called prostate specific membrane antigen (PSM) or human glutamate carboxypeptidase II (GCP II), EC number 3.4.17.21. It is believed that NAALADase is a co-catalytic zinc/zinc metallopeptidase. NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Pharmaceutically acceptable carrier" refers to any carrier, diluent, excipient, suspending agent, lubricating agent, adjuvant, vehicle, delivery system, emulsifier, disintegrant, absorbent, preservative, surfactant, colorant, flavorant, or sweetener. For these purposes, the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal, and intracranial injection or infusion techniques.

"Pharmaceutically acceptable equivalent" includes, without limitation, pharmaceutically acceptable salts, hydrates, metabolites, prodrugs, and isosteres. Many pharmaceutically acceptable equivalents are expected to have the same or similar in vitro or in vivo activity as the compounds of the invention.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Prodrug" refers to a derivative of the inventive compounds which undergoes biotransformation prior to exhibiting its pharmacological effect(s). A prodrug form is one which is not in an active form of the molecule as administered, but which becomes therapeutically active after some in vivo activity or biotransformation, such as metabolism, for example, enzymatic or hydrolytic cleavage. The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995).

"Radiosensitizer" refers to a low molecular weight compound administered to animals in therapeutically effective amounts to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention.

"Suramin (sodium salt)" refers to 8,8'-[carbonylbis[imino-3,1-phenylenecarbonylimino (4-methyl-3,1-phenylene)carbonylimino]]bis-1,3,5-naphthalenetrisulfonic acid hexasodium salt

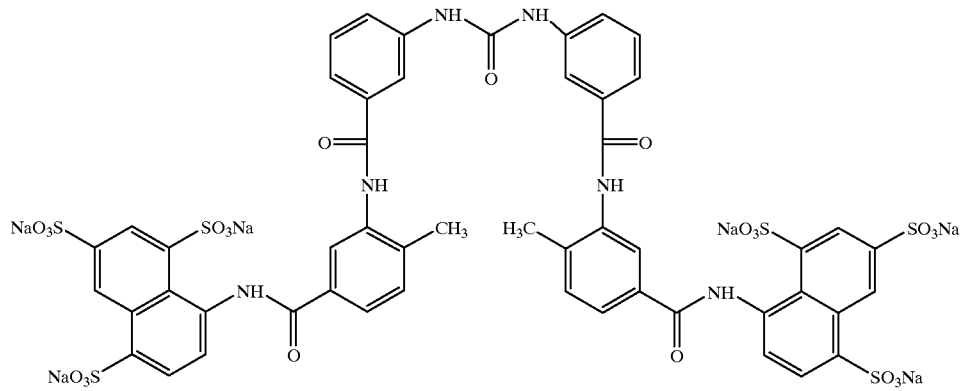

Suramin has known therapeutic uses as an antitrypanosomal and antifilarial agent. The compound also has known lethal characteristics, with a published $LD_{40}$ of 40 mg/kg in mice.

"Inhibition," in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ as used herein refers to the affinity between the inventive compounds and NAALADase. "$IC_{50}$" is a related term used to define the concentration or amount of a compound which is required to cause a 50% inhibition of the target enzyme. "NAALADase inhibitor" refers to any compound which inhibits NAALADase enzyme activity.

"Enantiomers" are a pair of stereoisomers that are non-superimposable mirror images of each other. "Enantiomer-enriched" refers to a mixture in which one enantiomer predominates.

"Isomers" refer to compounds having the same number and kind of atoms, and hence the same molecular weight, but differing in respect to the arrangement or configuration of the atoms.

"Optical isomers" refer to either of two kinds of stereoisomers. One kind is represented by mirror-image structures called enantiomers, which result from the presence of one or more asymmetric carbon atoms in the compound (glyceraldehyde, lactic acid, sugars, tartaric acid, amino acids). The other kind is exemplified by diastereoisomers, which are not mirror images. These occur in compounds having two or more asymmetric carbon atoms; thus, such compounds have $2_n$ optical isomers, where n is the number of asymmetric carbon atoms.

"Stereoisomers" are isomers that differ only in the arrangement of the atoms in space. "Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

"Angiogenesis" refers to the process whereby new capillaries are formed.

"Angiogenesis-dependent disease" includes without limitation rheumatoid arthritis, cardiovascular disease, neovascular diseases of the eye, peripheral vascular disorders, and dermatologic ulcers. "Inhibition" of angiogenesis may be measured by many parameters in accordance with the present invention and, for instance, may be assessed by delayed appearance of neovascular structures, slowed development of neovascular structures, decreased occurrence of neovascular structures, slowed or decreased severity of angiogenesis-dependent disease effects, arrested angiogenic growth, or regression of previous angiogenic growth. In the extreme, complete inhibition is referred to herein as prevention. In relation to angiogenesis or angiogenic growth, "prevention" refers to no substantial angiogenesis or angiogenic growth if none had previously occurred, or no substantial further angiogenesis or angiogenic growth if growth had previously occurred.

"Animal" refers to a living organism having sensation and the power of voluntary movement, and which requires for its existence oxygen and organic food. Examples include, without limitation, an animal such as a member of the human, equine, porcine, bovine, murine, canine, or feline species. In the case of a human, an "animal" may also be referred to as a "patient".

"Anxiety" includes without limitation the unpleasant emotion state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension. *Dorland's Illustrated Medical Dictionary*, W. B. Saunders Co., 27th ed. (1988).

"Anxiety Disorder" includes without limitation mental disorders in which anxiety and avoidance behavior predominate. *Dorland's Illustrated Medical Dictionary*, W. B. Saunders Co., 27th ed. (1988). Examples include without limitation panic attack, agoraphobia, panic disorder, acute stress disorder, chronic stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS. Other anxiety disorders are characterized in *Diagnostic and Statistical Manual of Mental Disorders* (American Psychiatric Association 4th ed. 1994). The skilled artisan will recognize that there are alternative nomenclatures, nosologies, and classification systems for pathologic psychological conditions and that these systems evolve with medical scientific progress.

"Attention Deficit Disorder" or "ADD" refers to a disorder characterized by developmentally inappropriate inattention and impulsiveness, with or without hyperactivity. Inattention means a failure to finish tasks started, easily distracted, seeming lack of attention, and difficulty concentrating on tasks requiring sustained attention. Impulsiveness means acting before thinking, difficulty taking turns, problems organizing work, and constant shifting from one activity to another. Hyperactivity means difficulty staying seated and sitting still, and running or climbing excessively.

"Cancer" includes without limitation ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

"CNS neurodegenerative disorder" refers to Alzheimer's disease, multiple sclerosis, the effects of stroke, CNS trauma (head injury), and any other disorders intended to be encompassed by this phrase as used in International Publication No. WO 98/03178.

"Compulsive disorder" refers to any disorder characterized by irresistible impulsive behavior. Examples of compulsive disorders include without limitation drug dependence, eating disorders, pathological gambling, Attention Deficit Disorder (ADD), and Tourette's syndrome.

"Demyelinating disease", refers to any disease involving damage to or removal of the myelin sheath naturally surrounding nerve tissue, such as that defined in U.S. Pat. No. 5,859,046 and International Publication No. WO 98/03178, herein incorporated by reference. Examples include without limitation peripheral demyelinating diseases (such as Guillain Barre syndrome, peripheral neuropathies and Charcot-Marie Tooth disease) and central demyelinating diseases (such as multiple sclerosis).

"Disease" refers to any deviation from or interruption of the normal structure or function of any part, organ, or system (or combinations) of the body that is manifested by a characteristic set of symptoms and signs and whose etiology, pathology, and prognosis may be known or unknown. *Dorland's Illustrated Medical Dictionary*, (W. B. Saunders Co. 27th ed. 1988).

"Disorder" refers to any derangement or abnormality of function; a morbid physical or mental state. *Dorland's Illustrated Medical Dictionary*, (W. B. Saunders Co. 27th ed. 1988).

"Drug dependence" refers to a psychologic addiction or a physical tolerance to a drug. Tolerance means a need to increase the dose progressively in order to produce the effect originally achieved by smaller amounts.

"Eating disorder" refers to compulsive overeating, obesity or severe obesity. obesity means body weight of 20% over standard height-weight tables. Severe obesity means over 100% overweight.

"Glutamate abnormality" refers to any "disease, disorder, or condition" in which glutamate is implicated, including pathological conditions involving elevated levels of glutamate. Examples of glutamate abnormalities include, without limitation, spinal cord injury, epilepsy, stroke, Alzheimer's disease, Parkinson's disease, Amyotrophic Lateral Sclerosis (ALS), Huntington's disease, schizophrenia, pain, ischemia, peripheral neuropathy (including but not limited to diabetic neuropathy), traumatic brain injury, neuronal insult, inflammatory diseases, anxiety, anxiety disorders, memory impairment, and compulsive disorders.

"Ischemia" refers to localized tissue anemia due to obstruction of the inflow of arterial blood. Global ischemia occurs when blood flow ceases for a period of time, such as may result from cardiac arrest. Focal ischemia occurs when a portion of the body, such as the brain, is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, drug intoxications and neurodegenerative diseases. For example, memory impairment is a common feature of neurodegenerative diseases such as Alzheimer's disease and senile dementia of the Alzheimer type. Memory impairment also occurs with other kinds of dementia such as multi-infarct dementia, a senile dementia caused by cerebrovascular deficiency, and the Lewy-body variant of Alzheimer's disease with or without association with Parkinson's disease. Creutzfeldt-Jakob disease is a rare dementia with which memory impairment is associated. It is a spongiform encephalopathy caused by the prion protein; it may be transmitted from other sufferers or may arise from gene mutations. Loss of memory is also a common feature of brain-damaged patients. Brain damage may occur, for example, after a classical stroke or as a result of an anaesthetic accident, head trauma, hypoglycemia, carbon monoxide poisoning, lithium intoxication, vitamin (B1, thiamine and $B_{12}$) deficiency, or excessive alcohol use. Korsakoff's amnesic psychosis is a rare disorder characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy.

"Mental disorder" refers to any clinically significant behavioral or psychological syndrome characterized by the presence of distressing symptoms or significant impairment of functioning. Mental disorders are assumed to result from some psychological or organic dysfunction of the individual; the concept does not include disturbances that are essentially conflicts between the individual and society (social deviance).

"Metastasis" refers to "[t]he ability of cells of a cancer to disseminate and form new foci of growth at noncontiguous sites (i.e., to form metastases)." See Hill, R. P, Chapter 11, "Metastasis", pp. 178–195 in *The Basic Science of Oncology*, Tannock et al., Eds., McGraw-Hill, New York (1992), herein incorporated by reference. "The transition from in situ tumor growth to metastatic disease is defined by the ability of tumor cells of the primary site to invade local tissues and to cross tissue barriers . . . To initiate the metastatic process, carcinoma cells must first penetrate the epithelial basement membrane and then invade the interstitial stroma . . . For distant metastases, intravasation requires tumor cell invasion of the subendothelial basement membrane that must also be negotiated during tumor cell extravasation . . . The development of malignancy is also associated with tumor-induced angiogenesis [which] not only allows for expansion of the primary tumors, but also permits easy access to the vascular compartment due to defects in the basement membranes of newly formed vessels." See Aznavoorian et al., *Cancer* 71: 1368–1383 (1993), herein incorporated by reference.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination processes, epilepsy, cognitive disorder, glutamate abnormality and secondary effects thereof. Currently, there is no known effective treatment for nervous tissue damage.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

"Neuroprotective" refers to the effect of reducing, arresting or ameliorating nervous insult, and protecting, resuscitating or reviving nervous tissue which has suffered nervous insult.

"Pain" refers to localized sensations of discomfort, distress or agony, resulting from the stimulation of specialized nerve endings. It serves as a protective mechanism insofar as it induces the sufferer to remove or withdraw from the source. *Dorland's Illustrated Medical Dictionary*, (W. B. Saunders Co. 27th ed. 1988). Examples of pain include, without limitation, acute, chronic, cancer, burn, incisional, inflammatory, diabetic neuropathic and back pain.

"Pathological gambling" refers to a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Prostate disease" refers to any disease affecting the prostate. Examples of prostate disease include without limitation prostate cancer such as adenocarcinoma and metastatic cancers of the prostate; and conditions characterized by abnormal growth of prostatic epithelial cells such as benign prostatic hyperplasia.

"Schizophrenia" refers to a mental disorder or group mental disorders characterized by disturbances in form and content of thought (loosening of associations, delusions, hallucinations), mood (blunted, flattened, inappropriate affect), sense of self and relationship to the external world (loss of ego boundaries, dereistic thinking, and autistic withdrawal), and behavior (bizarre, apparently purposeless, and stereotyped activity or inactivity). Examples of schizophrenia include, without limitation, acute, ambulatory, borderline, catatonic, childhood, disorganized, hebephrenic, latent, nuclear, paranoid, paraphrenic, prepsychotic, process, pseudoneurotic, pseudopsychopathic, reactive, residual, schizo-affective and undifferentiated schizophrenia. *Dorland's Illustrated Medical Dictionary*, (W. B. Saunders Co. 27th ed. 1988).

"Therapeutic window of opportunity" or "window" refers, in relation to stroke, to the maximal delay between the onset of stroke and the initiation of efficacious therapy.

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

"Treating" or "treatment" as used herein covers any treatment of a disease and/or condition in an animal, particularly a human, and includes:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

In relation to drug dependence, "treating" includes administering a compound or composition of the present invention to suppress the psychologic addiction or physical tolerance to the drug of abuse, and/or relieve and/or prevent a withdrawal syndrome resulting from the drug dependence.

"Withdrawal syndrome" refers to a disorder characterized by untoward physical changes that occur when the drug is discontinued or when its effect is counteracted by a specific antagonist.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

METHODS OF THE PRESENT INVENTION

The present invention relates to various methods of using a compound of formula I

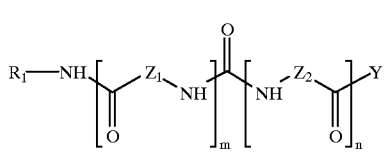

or a pharmaceutically acceptable equivalent, wherein:

m and n are independently 0, 1, 2 or 3;

Y is —$R_2$ or —$NHR_2$;

$R_1$ and $R_2$ are independently an aryl or heteroaryl group substituted with one or more substituent(s);

$Z_1$ and $Z_2$ are independently a moiety of formula II, III or IV

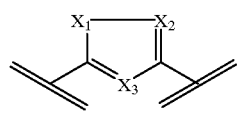

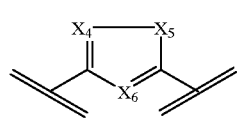

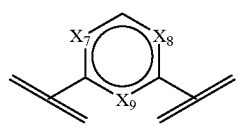

$X_1$ and $X_5$ are independently $CHR_3$ or $NR_3$;

$X_2$, $X_3$, $X_4$, $X_6$, $X_7$, $X_8$ and $X_9$ are independently $CR_3$ or N; and $R_3$ is H or $CH_3$.

$Z_1$, $Z_2$, $X_1$, $X_2$, $X_3$, $X_4$, $X_5$ and $X_6$ are independently selected at each occurrence within a compound. When m is 2, for example, formula I would have two $Z_1$ moieties which may differ from each other, with the first $Z_1$ being a moiety of formula II with $X_1$, $X_2$ and $X_3$ each being $CHR_3$, and the second $Z_1$ being either a moiety of formula III or IV, or a moiety of formula II with $X_1$, $X_2$ and $X_3$ each being $NR_3$.

Useful aryl groups include without limitation phenyl, naphthyl, anthracenyl and phenanthryl. Useful heteroaryl groups include without limitation furanyl, pyrrolyl, thiophenyl, imidazolyl, oxazolyl, thiazolyl, pyridyl, pyrimidinyl, quinolinyl and isoquinolinyl.

Possible substituents of said aryl or heteroaryl group include, without limitation, $C_2$–$C_9$ straight or branched chain alkyl, $C_2$–$C_9$ straight or branched chain alkenyl, $C_1$–$C_9$ alkoxy, $C_2$–$C_9$ alkenyloxy, phenoxy, benzyloxy, $C_3$–$C_8$ cycloalkyl, $C_2$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include, without limitation, phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl.

In one embodiment, m and n are independently 1, 2 or 3; Y is —$NHR_2$; and $R_1$ and $R_2$ are independently an aryl group substituted with one or more sulfonic acid group(s). Preferably, $R_1$ and $R_2$ are independently a naphthyl group substituted with 1, 2 or 3 sulfonic acid group(s). When the naphthyl group is substituted with 3 sulfonic acid groups, the sulfonic acid substituents are preferably in the 1-, 3- and 5-, or 1-, 3- and 6-positions. When it is substituted with 2 sulfonic acid groups, the sulfonic acid substituents are preferably in the 1- and 3-, 1- and 5-, 3- and 5-, or 3- and 6-positions. When it is substituted with 1 sulfonic acid group, the sulfonic acid substituent is preferably in the 1-, 3- or 5-position.

More preferably, m and n are independently 1 or 2; $Z_1$ and $Z_2$ are independently a moiety of formula II or III; $X_1$ and $X_5$ are each $NCH_3$; and $X_2$, $X_3$, $X_4$, $X_6$, $X_7$, $X_8$ and $X_9$ are each CH.

Alternatively, m and n are independently 1 or 2; $Z_1$ and $Z_2$ are each a moiety of formula IV; and $X_7$, $X_8$ and $X_9$ are each CH.

Preferred compounds of this embodiment may be selected from the group consisting of:
suramin;
2,2'-(carbonyl-bis(imino-N-methyl-4,2-pyrrolecarbonylimino(N-methyl-4,2-pyrrole)carbonylimino))bis(1,5-naphthalenedisulfonic acid);
8,8'-[carbonylbis(imino-3,1-phenylene)]bis-(1,3,5-naphthalenetrisulfonic acid);
5-[[[1-methyl-4-[[[[1-methyl-6-[[(4,5,7-trisulfo-1-naphthalenyl)amino]carbonyl]-1H-pyrrol-3-yl]amino]carbonyl]amino]-1H-pyrrol-2-yl]carbonyl]amino]-1,3,8-naphthalenetrisulfonic acid;
4-[[[1-methyl-4-[[[[1-methyl-5- [[(4-sulfo-1-naphthalenyl)amino]carbonyl]-1H-pyrrol-3-yl]amino]carbonyl]amino]-1H-pyrrol-2-yl]carbonyl]amino]-1-naphthalenesulfonic acid;
7,7'-(carbonyl-bis(imino-N-methyl-4,2-pyrrolecarbonylimino(N-methyl-4,2-pyrrole)carbonylimino))bis(3,5-naphthalenedisulfonic acid);
7,7'-(carbonyl-bis(imino-N-methyl-4,2-pyrrolecarbonylimino(N-methyl-4,2-pyrrole)carbonylimino))bis(3,6-naphthalenedisulfonic acid);
7,7'-(carbonyl-bis(imino-N-methyl-4,2-pyrrolecarbonylimino(N-methyl-4,2-pyrrole)carbonylimino))bis(1,3,5-naphthalenetrisulfonic acid);
8,8'-(carbonyl-bis(imino-N-methyl-4,2-pyrrolecarbonylimino(N-methyl-4,2-pyrrole)carbonylimino))bis(1,3,6-naphthalenetrisulfonic acid);
7,7'-(carbonyl-bis(imino-N-methyl-4,2-pyrrolecarbonylimino(N-methyl-4,2-pyrrole)carbonylimino))bis(1,3-naphthalenedisulfonic acid);
7,7'-(carbonyl-bis(imino-N-methyl-4,2-pyrrolecarbonylimino(N-methyl-4,2-pyrrole)carbonylimino))bis(2,4-naphthalenedisulfonic acid);
8,8'-(carbonyl-bis(imino-N-methyl-4,2-pyrrolecarbonylimino(N-methyl-4,2-pyrrole)carbonylimino))bis(2,4-naphthalenedisulfonic acid);
8,8'-(carbonyl-bis(imino-N-methyl-4,2-pyrrolecarbonylimino(N-methyl-4,2-pyrrole)carbonylimino))bis(1,3,5-naphthalenetrisulfonic acid);
8,8'-(carbonyl-bis(imino-N-methyl-4,2-pyrrolecarbonylimino(N-methyl-4,2-pyrrole)carbonylimino))bis(5-naphthalenesulfonic acid);
8,8'-(carbonyl-bis(imino-N-methyl-4,2-pyrrolecarbonylimino(N-methyl-4,2-pyrrole)carbonylimino))bis(1,3-naphthalenedisulfonic acid);
8,8'-(carbonyl-bis(imino-N-methyl-4,2-pyrrolecarbonylimino(N-methyl-4,2-pyrrole)carbonylimino))bis(3,5-naphthalenedisulfonic acid);
8,8'-(carbonyl-bis(imino-N-methyl-4,2-pyrrolecarbonylimino(N-methyl-4,2-pyrrole)carbonylimino))bis(1,5-naphthalenedisulfonic acid);
8,8'-(carbonyl-bis(imino-N-methyl-4,2-pyrrolecarbonylimino(N-methyl-4,2-pyrrole)carbonylimino))bis(3-naphthalenesulfonic acid);
8,8'-(carbonyl-bis(imino-N-methyl-4,2-pyrrolecarbonylimino(N-methyl-4,2-pyrrole)carbonylimino))bis(1-naphthalenesulfonic acid);
7,7'-(carbonyl-bis(imino-N-methyl-4,2-pyrrolecarbonylimino(N-methyl-4,2-pyrrole)carbonylimino))bis(1,6-naphthalenedisulfonic acid);
7,7'-(carbonyl-bis(imino-N-methyl-4,2-pyrrolecarbonylimino(N-methyl-4,2-pyrrole)carbonylimino))bis(2,6-naphthalenedisulfonic acid);
7,7'-(carbonyl-bis(imino-N-methyl-4,2-pyrrolecarbonylimino(N-methyl-4,2-pyrrole)carbonylimino))bis(1,5-naphthalenedisulfonic acid);
7,7'-(carbonyl-bis(imino-N-methyl-4,2-pyrrolecarbonylimino(N-methyl-4,2-pyrrole)carbonylimino))bis(2,5-naphthalenedisulfonic acid);
7,7'-(carbonyl-bis(imino-N-methyl-4,2-pyrrolecarbonylimino(N-methyl-4,2-pyrrole)carbonylimino))bis(2,3-naphthalenedisulfonic acid);
8,8'-(carbonyl-bis(imino-N-methyl-4,2-pyrrolecarbonylimino(N-methyl-4,2-pyrrole)carbonylimino))bis(1,6-naphthalenedisulfonic acid);
8,8'-(carbonyl-bis(imino-N-methyl-4,2-pyrrolecarbonylimino(N-methyl-4,2-pyrrole)carbonylimino))bis(2,6-naphthalenedisulfonic acid);
8,8'-(carbonyl-bis(imino-N-methyl-4,2-pyrrolecarbonylimino(N-methyl-4,2-pyrrole)carbonylimino))bis(2,5-naphthalenedisulfonic acid);
8,8'-(carbonyl-bis(imino-N-methyl-4,2-pyrrolecarbonylimino(N-methyl-4,2-pyrrole)carbonylimino))bis(3,6-naphthalenedisulfonic acid);
8,8'-(carbonyl-bis(imino-N-methyl-4,2-pyrrolecarbonylimino(N-methyl-4,2-pyrrole)carbonylimino))bis(2,3,5-naphthalenetrisulfonic acid);
8,8'-(carbonyl-bis(imino-N-methyl-4,2-pyrrolecarbonylimino(N-methyl-4,2-pyrrole)carbonylimino))bis(1,4,6-naphthalenetrisulfonic acid);
8,8'-(carbonyl-bis(imino-N-methyl-4,2-pyrrolecarbonylimino(N-methyl-4,2-pyrrole)carbonylimino))bis(2,4,6-naphthalenetrisulfonic acid);

7,7'-(carbonyl-bis(imino-N-methyl-4,2-pyrrolecarbonylimino(N-methyl-4,2-pyrrole)carbonylimino))bis(1-naphthalenesulfonic acid);

7,7'-(carbonyl-bis(imino-N-methyl-4,2-pyrrolecarbonylimino(N-methyl-4,2-pyrrole)carbonylimino))bis(2-naphthalenesulfonic acid);

7,7'-(carbonyl-bis(imino-N-methyl-4,2-pyrrolecarbonylimino(N-methyl-4,2-pyrrole)carbonylimino))bis(3-naphthalenesulfonic acid);

7,7'-(carbonyl-bis(imino-N-methyl-4,2-pyrrolecarbonylimino(N-methyl-4,2-pyrrole)carbonylimino))bis(4-naphthalenesulfonic acid);

7,7'-(carbonyl-bis(imino-N-methyl-4,2-pyrrolecarbonylimino(N-methyl-4,2-pyrrole)carbonylimino))bis(1,4,6-naphthalenetrisulfonic acid);

7,7'-(carbonyl-bis(imino-N-methyl-4,2-pyrrolecarbonylimino(N-methyl-4,2-pyrrole)carbonylimino))bis(1,3,6-naphthalenetrisulfonic acid);

7,7'-(carbonyl-bis(imino-N-methyl-4,2-pyrrolecarbonylimino))bis(1,3-naphthalenedisulfonic acid);

7,7'-(carbonyl-bis(imino-N-methyl-4,2-pyrrolecarbonylimino(N-methyl-4,2-pyrrolecarbonylimino(N-methyl-4,2-pyrrole)carbonylimino))bis(1,3-naphthalenedisulfonicacid);

7,7'-(carbonyl-bis(imino-N-methyl-4,2-pyrrolecarbonylimino(N-methyl-4,2-pyrrole)carbonylimino))bis(2,4,6-naphthalenetrisulfonic acid);

7,7'-(carbonyl-bis(imino-N-methyl-4,2-pyrrolecarbonylimino(N-methyl-4,2-pyrrole)carbonylimino))bis(2,3,5-naphthalenetrisulfonic acid); and pharmaceutically acceptable equivalents.

The most preferred compounds of this embodiment are selected from the group consisting of:

suramin;

8,8'-[carbonylbis(imino-3,1-phenylene)]bis-(1,3,5-naphthalenetrisulfonic acid);

5-[[[1-methyl-4-[[[[1-methyl-6-[[(4,5,7-trisulfo-1-naphthalenyl)amino]carbonyl]-1H-pyrrol-3-yl]amino]carbonyl]amino]-1H-pyrrol-2-yl]carbonyl]amino]1,3,8-naphthalenetrisulfonic acid;

4-[[[1-methyl-4-[[[[1-methyl-5-[[(4-sulfo-1-naphthalenyl)amino]carbonyl]-1H-pyrrol-3-yl]amino]carbonyl]amino]-1H-pyrrol-2-yl]carbonyl]amino]-1-naphthalenesulfonic acid; and pharmaceutically acceptable equivalents.

In another embodiment, m and n are each 0; Y is —R$_2$; and R$_1$ is a naphthyl group substituted with 1, 2 or 3 sulfonic acid group(s).

A representative compound of this embodiment is 8-(3-nitrobenzamido)-1,3,5-naphthalenetrisulfonic acid or a pharmaceutically acceptable equivalent.

Some compounds of formula I possess one or more asymmetric carbon center(s) and are thus capable of existing in the form of optical isomers as well as in the form of racemic or non-racemic mixtures of optical isomers. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules, for example, esters, amides, acetals, ketals, and the like, by reacting compounds used in the inventive methods and pharmaceutical compositions with an optically active acid in an activated form, an optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the parent optically active drug is not necessary prior to dosing the patient since the compound can behave as a prodrug. The optically active compounds of the present invention can likewise be obtained by utilizing optically active starting materials.

It is understood that the compounds of formula I encompass optical isomers as well as racemic and non-racemic mixtures.

Methods For Inhibiting NAALADase Enzyme Activity

Specifically, the present invention relates to a method for inhibiting NAALADase enzyme activity, comprising administering to said mammal an effective amount of a compound of formula I, as defined above.

Methods For Treating Glutamate Abnormalities

The present invention further relates to a method for treating a glutamate abnormality in a mammal, comprising administering to said mammal an effective amount of a compound of formula I, as defined above.

Preferably, when m and n are independently 1, 2 or 3, Y is —NHR$_2$, R$_2$ is naphthyl substituted with 1, 2 or 3 sulfonic acid(s), Z$_1$ and Z$_2$ are each a moiety of formula II, X$_1$ and X$_2$ are each CH, X$_3$ is NR$_3$, and R$_3$ is CH$_3$, then the glutamate abnormality is not a demyelinating disease; and when the compound of formula I is suramin, then the glutamate abnormality is not a CNS neurodegenerative disorder or a demyelinating disease.

More preferably, the glutamate abnormality is selected from the group consisting of compulsive disorder, stroke, demyelinating disease, schizophrenia, Parkinson's disease, ALS, diabetic neuropathy, pain, anxiety, anxiety disorder and memory impairment.

Stroke patients often experience a significant temporal delay between the onset of ischemia and the time to initiation of therapy. Thus, there is a need for neuroprotectants with a long therapeutic window of opportunity. It is expected that the compounds of formula I have a therapeutic window of opportunity of at least 1 hour. Accordingly, when the glutamate abnormality is stroke, the compound of formula I may be administered to said mammal 60 minutes, 120 minutes or more following onset of stroke.

When the glutamate abnormality is pain, the compound of formula I is preferably administered in combination with an effective amount of morphine.

Although not limited to any one particular theory, it is believed that the compounds of formula I modulate levels of glutamate by acting on a storage form of glutamate which is hypothesized to be upstream from the effects mediated by the NMDA receptor.

Methods For Effecting Neuronal Activities

The present invention further relates to a method for effecting a neuronal activity in a mammal, comprising administering to said mammal an effective amount of a compound of formula I, as defined above.

Preferably, when m and n are independently 1, 2 or 3, Y is —$NHR_2$, $R_2$ is naphthyl substituted with 1, 2 or 3 sulfonic acid(s), $Z_1$ and $Z_2$ are each a moiety of formula II, $X_1$ and $X_2$ are each CH, $X_3$ is $NR_3$, and $R_3$ is $CH_3$, then the effecting a neuronal activity is not treating a demyelinating disease; and when the compound of formula I is suramin, then the effecting a neuronal activity is not treating a CNS neurodegenerative disorder or a demyelinating disease.

The neuronal activity that is effected by the inventive method may be selected from the group consisting of stimulation of damaged neurons, promotion of neuronal regeneration, prevention of neurodegeneration and treatment of a neurological disorder.

Examples of neurological disorders that are treatable by the methods of the present invention include without limitation: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barre syndrome; Alzheimer's disease; and Parkinson's disease.

The inventive method is particularly useful for treating a neurological disorder selected from the group consisting of peripheral neuropathy caused by physical injury or disease state, traumatic brain injury, physical damage to spinal cord, stroke associated with brain damage, demyelinating disease and neurological disorder relating to neurodegeneration.

Examples of neurological disorders relating to neurodegeneration include Alzheimer's disease, Parkinson's disease, and amyotrophic lateral sclerosis (ALS).

Methods For Treating Prostate Diseases

The present invention further relates to a method for treating a prostate disease in a mammal, comprising administering to said mammal an effective amount of a compound of formula I, as defined above.

Preferably, when the compound of formula I is suramin, then the prostate disease is not prostate cancer.

Methods For Treating Cancers

The present invention further relates to a method for treating cancer in a mammal, comprising administering to said mammal an effective amount of a compound of formula I, as defined above.

Preferably, when the compound of formula I is suramin, then the cancer is not prostate cancer.

Methods For Inhibiting Angiogenesis

The present invention further relates to a method for inhibiting angiogenesis in a mammal, comprising administering to said mammal an effective amount of a compound of formula I, as defined above.

Pharmaceutical Compositions of the Present Invention

The present invention also relates to a pharmaceutical composition comprising:
(i) an effective amount of a compound of formula I, as defined above; and
(ii) a pharmaceutically acceptable carrier.

Preferably, the compound of formula I is present in an effective amount for inhibiting NAALADase enzyme activity or angiogenesis, effecting a neuronal activity, or treating a glutamate abnormality, prostate disease or cancer in a mammal.

More preferably, when m and n are independently 1, 2 or 3, Y is —$NHR_2$, $Z_1$ and $Z_2$ are each a moiety of formula II, $X_1$ and $X_2$ are each CH, $X_3$ is $NR_3$, and $R_3$ is $CH_3$, then $R_2$ is not naphthyl substituted with 1, 2 or 3 sulfonic acid(s); and the compound of formula I is not suramin.

Route of Administration

In the inventive methods, the compounds will generally be administered to a patient in the form of a pharmaceutical formulation. Such formulation preferably includes, in addition to the active agent, a physiologically acceptable carrier and/or diluent. The compounds may be administered by any means known to an ordinarily skilled artisan. For example, the compounds may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal, intracranial or intraosseous injection and infusion techniques.

To be effective therapeutically as central nervous system targets, the compounds should readily penetrate the blood-brain barrier when peripherally administered. Compounds which cannot penetrate the blood-brain barrier can be effectively administered by an intraventricular route.

Dosage

The compounds and compositions of the present invention may be administered by a single dose, multiple discrete doses or continuous infusion. The compounds are well suited to continuous infusion. Pump means, particularly subcutaneous pump means, are preferred for continuous infusion.

Dose levels on the order of about 0.1 mg to about 10,000 mg of the active ingredient compound, but less than 40 mg/kg where the compound is Suramin, are useful in the treatment of the above conditions, with preferred levels being about 0.1 mg to about 1,000 mg. The specific dose level for any particular patient will vary depending upon a variety of factors, including the activity and the possible toxicity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

Administration Regimen

For the methods of the present invention, any administration regimen well known to an ordinarily skilled artisan for regulating the timing and sequence of drug delivery can be used and repeated as necessary to effect treatment. Such regimen may include pretreatment and/or co-administration with additional therapeutic agents.

Co-Administration With Other Treatments

The compounds and compositions of the present invention may be used alone or in combination with one or more additional agent(s) for simultaneous, separate or sequential use.

The additional agent(s) may be any therapeutic agent(s) known to an ordinarily skilled artisan, including without limitation: one or more compound(s) of formula I; steroids, for example, hydrocortisomes such as methylprednisolone; anti-inflammatory or anti-immune drugs, such as methotrexate, azathioprine, cyclophosphamide or cyclosporin A; interferon-β; antibodies, such as anti-CD4 antibodies; agents which can reduce the risk of a second ischemic event, such as ticlopidine; chemotherapeutic agents; immunotherapeutic compositions; electromagnetic radiosensitizers; and morphine.

The compounds of the present invention can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a compound of the present invention, as well as one or more pharmaceutical excipients, such as wetting, emulsifying and pH buffering agents.

EXAMPLES

The following examples are illustrative of the present invention and are not intended to be limitations thereon.

Example 1
In Vitro Inhibition of NAALADase Activity

Various compounds of formula I were tested for in vitro inhibition of NAALADase activity, and the results are provided below in TABLE I.

TABLE I

| IN VITRO INHIBITION OF NAALADASE ACTIVITY | |
|---|---|
| Compound | $K_1$ (nM) |
| Suramin, sodium salt | 527 |
| 8-(3-nitrobenzamido)-1,3,5-naphthalenetrisulfonic acid | 20,200 |
| 8,8'-[carbonylbis(imino-3,1-phenylene)]bis-(1,3,5-naphthalene-trisulfonic acid), sodium salt | 188 |

Protocol For Assaying In Vitro Inhibition of NAALADase Activity

The following were combined in each assay tube: 100 μL of 10 mM $CoCl_2$, 250 μL of 200 mM Tris chloride, 100 μL tissue, 100 μL of 10 mM NAALADase inhibitor in Bakers $H_2O$, and Bakers $H_2O$ to make a total volume of 950 μL. Each tube was then incubated for 10 minutes in a 37° C. water bath. 50 μL of 3-H-NAAG was then added to each assay tube and incubated for an additional 15 minutes in a 37° C. water bath. The assay was stopped by adding 1.0 ml of 0.1 M sodium phosphate.

Glutamate released by the action of the NAALADase enzyme was separated from the assay solution using an anion exchange resin. The resin was equilibrated to 25° C., 2.0 ml of the resin was added to a Pasteur pipette pre-loaded with a single glass bead, and each column was washed twice with distilled $H_2O$. A column was placed over a scintillation vial and 200 μL of an assay sample was loaded onto the column. After draining, glutamate was eluted using two 1.0 ml washes of 1 M formic acid. After addition of 10 ml of scintillation cocktail, each sample was counted for 2 minutes on a scintillation counter.

Example 2
In Vitro Assay on Ischemia

To examine the in vitro effect of the compounds of formula I on ischemia, cortical cell cultures were treated with various compounds of formula I during an ischemic insult utilizing potassium cyanide and 2-deoxyglucose, and for one hour thereafter (for experimental details, see Vornov et al., *J. Neurochem.*, Vol. 65, No. 4, pp. 1681–1691 (1995)). The results are provided below in TABLE II and graphically presented in FIG. 1A, B, and C. Neuroprotective effect is expressed as $EC_{50}$, the concentration of the compound which is required to cause a 50% reduction in glutamate toxicity following an ischemic insult.

TABLE II

| Compound | $EC_{50}$ (nM) |
|---|---|
| Suramin, sodium salt | 24.7 |
| 8-(3-nitrobenzamido)-1,3,5-naphthalenetrisulfonic acid | >1000 |
| 8,8'-[carbonylbis(imino-3,1-phenylene)]bis-(1,3,5-naphthalene-trisulfonic acid), sodium salt | 14.1 |

Example 3

A patient is suffering from a disease, disorder or condition described above. The patient may then be administered an effective amount of Suramin, sodium salt; of 8-(3-nitrobenzamido)-1,3,5-naphthalenetrisulfonic acid; or of 8,8'-[carbonylbis(imino-3,1-phenylene)]bis-(1,3,5-naphthalenetrisulfonic acid), sodium salt. It is expected that after such treatment, the patient would not suffer any significant injury due to, would be protected from further injury due to, or would recover from the disease, disorder or condition.

The invention being thus described, it will be obvious that the same may be varied in many ways. Such variations are not to be regarded as a departure from the spirit and scope of the invention and all such modifications are intended to be included within the scope of the following claims.

We claim:

1. A method for inhibiting NAALADase enzyme activity in a mammal, comprising administering to a mammal in need thereof an effective amount of a compound of formula I

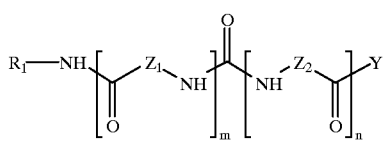

or a pharmaceutically acceptable equivalent, wherein:

m and n are independently 0, 1, 2 or 3;

Y is $-R_2$ or $-NHR_2$;

$R_1$ and $R_2$ are independently an aryl or heteroaryl group substituted with one or more substituent(s);

$Z_1$ and $Z_2$ are independently a moiety of formula II, III or IV

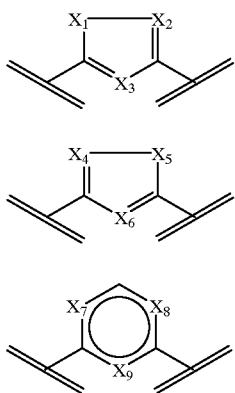

$X_1$ and $X_5$ are independently $CHR_3$ or $NR_3$;
$X_2$, $X_3$, $X_4$, $X_6$, $X_7$, $X_8$ and $X_9$ are independently $CR_3$ or N; and
$R_3$ is H or $CH_3$.

2. The method of claim 1, wherein:
m and n are independently 1, 2 or 3;
Y is —$NH_2$; and
$R_1$ and $R_2$ are independently an aryl group substituted with one or more sulfonic acid group(s).

3. The method of claim 2, wherein $R_1$ and $R_2$ are independently a naphthyl group substituted with 1, 2 or 3 sulfonic acid group(s).

4. The method of claim 3, wherein:
m and n are independently 1 or 2;
$Z_1$ and $Z_2$ are independently a moiety of formula II or III;
$X_1$ and $X_5$ are each $NCH_3$; and
$X_2$, $X_3$, $X_4$, $X_6$, $X_7$, $X_8$ and $X_9$ are each CH.

5. The method of claim 3, wherein:
m and n are independently 1 or 2;
$Z_1$ and $Z_2$ are each a moiety of formula IV; and
$X_7$, $X_8$ and $X_9$ are each CH.

6. The method of claim 2, wherein the compound of formula I is selected from the group consisting of:
suramin;
2,2'-(carbonyl-bis(imino-N-methyl-4,2-pyrrolecarbonylimino(N-methyl-4,2-pyrrole)carbonylimino))bis(1,5-naphthalenedisulfonic acid);
8,8'-[carbonylbis(imino-3,1-phenylene)]bis-(1,3,5-naphthalenetrisulfonic acid);
5-[[[1-methyl-4-[[[[1-methyl-6-[[(4,5,7-trisulfo-1-naphthalenyl)amino]carbonyl]-1H-pyrrol-3-yl]amino]carbonyl]amino]-1H-pyrrol-2-yl]carbonyl]amino]1,3,8-naphthalenetrisulfonic acid;
4-[[[1-methyl-4-[[[[1-methyl-5-[[(4-sulfo-1-naphthalenyl)amino]carbonyl]-1 H-pyrrol-3-yl]amino]carbonyl]amino]-1H-pyrrol-2-yl]carbonyl]amino]1-naphthalenesulfonic acid;
7,7'-(carbonyl-bis(imino-N-methyl-4,2-pyrrolecarbonylimino(N-methyl-4,2-pyrrole)carbonylimino))bis(3,5-naphthalenedisulfonic acid);
7,7'-(carbonyl-bis(imino-N-methyl-4,2-pyrrolecarbonylimino(N-methyl-4,2-pyrrole)carbonylimino))bis(3,6-naphthalenedisulfonic acid);
7,7'-(carbonyl-bis(imino-N-methyl-4,2-pyrrolecarbonylimino(N-methyl-4,2-pyrrole)carbonylimino))bis(1,3,5-naphthalenetrisulfonic acid);
8,8'-(carbonyl-bis(imino-N-methyl-4,2-pyrrolecarbonylimino(N-methyl-4,2-pyrrole)carbonylimino))bis(1,3,6-naphthalenetrisulfonic acid);
7,7'-(carbonyl-bis(imino-N-methyl-4,2-pyrrolecarbonylimino(N-methyl-4,2-pyrrole)carbonylimino))bis(1,3-naphthalenedisulfonic acid);
7,7'-(carbonyl-bis(imino-N-methyl-4,2-pyrrolecarbonylimino(N-methyl-4,2-pyrrole)carbonylimino))bis(2,4-naphthalenedisulfonic acid);
8,8'-(carbonyl-bis(imino-N-methyl-4,2-pyrrolecarbonylimino(N-methyl-4,2-pyrrole)carbonylimino))bis(2,4-naphthalenedisulfonic acid);
8,8'-(carbonyl-bis(imino-N-methyl-4,2-pyrrolecarbonylimino(N-methyl-4,2-pyrrole)carbonylimino))bis(1,3,5-naphthalenetrisulfonic acid);
8,8'-(carbonyl-bis(imino-N-methyl-4,2-pyrrolecarbonylimino(N-methyl-4,2-pyrrole)carbonylimino))bis(5-naphthalenesulfonic acid);
8,8'-(carbonyl-bis(imino-N-methyl-4,2-pyrrolecarbonylimino(N-methyl-4,2-pyrrole)carbonylimino))bis(1,3-naphthalenedisulfonic acid);
8,8'-(carbonyl-bis(imino-N-methyl-4,2-pyrrolecarbonylimino(N-methyl-4,2-pyrrole)carbonylimino))bis(3,5-naphthalenedisulfonic acid);
8,8'-(carbonyl-bis(imino-N-methyl-4,2-pyrrolecarbonylimino(N-methyl-4,2-pyrrole)carbonylimino))bis(1,5-naphthalenedisulfonic acid);
8,8'-(carbonyl-bis(imino-N-methyl-4,2-pyrrolecarbonylimino(N-methyl-4,2-pyrrole)carbonylimino))bis(3-naphthalenesulfonic acid);
8,8'-(carbonyl-bis(imino-N-methyl-4,2-pyrrolecarbonylimino(N-methyl-4,2-pyrrole)carbonylimino))bis(1-naphthalenesulfonic acid);
7,7'-(carbonyl-bis(imino-N-methyl-4,2-pyrrolecarbonylimino(N-methyl-4,2-pyrrole)carbonylimino))bis(1,6-naphthalenedisulfonic acid);
7,7'-(carbonyl-bis(imino-N-methyl-4,2-pyrrolecarbonylimino(N-methyl-4,2-pyrrole)carbonylimino))bis(2,6-naphthalenedisulfonic acid);
7,7'-(carbonyl-bis(imino-N-methyl-4,2-pyrrolecarbonylimino(N-methyl-4,2-pyrrole)carbonylimino))bis(1,5-naphthalenedisulfonic acid);
7,7'-(carbonyl-bis(imino-N-methyl-4,2-pyrrolecarbonylimino(N-methyl-4,2-pyrrole)carbonylimino))bis(2,5-naphthalenedisulfonic acid);
7,7'-(carbonyl-bis(imino-N-methyl-4,2-pyrrolecarbonylimino(N-methyl-4,2-pyrrole)carbonylimino))bis(2,3-naphthalenedisulfonic acid);
8,8'-(carbonyl-bis(imino-N-methyl-4,2-pyrroe)carbonylimino))bis(1,6-naphthalenedisulfonic acid);
8,8'-(carbonyl-bis(imino-N-methyl-4,2-pyrrolecarbonylimino(N-methyl-4,2-pyrrole)carbonylimino))bis(2,6-naphthalenedisulfonic acid);
8,8'-(carbonyl-bis(imino-N-methyl-4,2-pyrrolecarbonylimino(N-methyl-4,2-pyrrole)carbonylimino))bis(2,5-naphthalenedisulfonic acid);
8,8'-(carbonyl-bis(imino-N-methyl-4,2-pyrrolecarbonylimino(N-methyl-4,2-pyrrole)carbonylimino))bis(3,6-naphthalenedisulfonic acid);
8,8'-(carbonyl-bis(imino-N-methyl-4,2-pyrrolecarbonylimino(N-methyl-4,2-pyrrole)carbonylimino))bis(2,3,5-naphthalenetrisulfonic acid);
8,8'-(carbonyl-bis(imino-N-methyl-4,2-pyrrolecarbonylimino(N-methyl-4,2-pyrrole)carbonylimino))bis(1,4,6-naphthalenetrisulfonic acid);
8,8'-(carbonyl-bis(imino-N-methyl-4,2-pyrrolecarbonylimino(N-methyl-4,2-pyrrole)carbonylimino))bis(2,4,6-naphthalenetrisulfonic acid);
7,7'-(carbonyl-bis(imino-N-methyl-4,2-pyrrolecarbonylimino(N-methyl-4,2-pyrrole)carbonylimino))bis(1-naphthalenesulfonic acid);

7,7'-(carbonyl-bis(imino-N-methyl-4,2-pyrrolecarbonylimino(N-methyl-4,2-pyrrole)carbonylimino))bis(2-naphthalenesulfonic acid);

7,7'-(carbonyl-bis(imino-N-methyl-4,2-pyrrolecarbonylimino(N-methyl-4,2-pyrrole)carbonylimino))bis(3-naphthalenesulfonic acid);

7,7'-(carbonyl-bis(imino-N-methyl-4,2-pyrrolecarbonylimino(N-methyl-4,2-pyrrole)carbonylimino))bis(4-naphthalenesulfonic acid);

7,7'-(carbonyl-bis(imino-N-methyl-4,2-pyrrolecarbonylimino(N-methyl-4,2-pyrrole)carbonylimino))bis(1,4,6-naphthalenetrisulfonic acid);

7,7'-(carbonyl-bis(imino-N-methyl-4,2-pyrrolecarbonylimino(N-methyl-4,2-pyrrole)carbonylimino))bis(1,3,6-naphthalenetrisulfonic acid);

7,7'-(carbonyl-bis(imino-N-methyl-4,2-pyrrolecarbonylimino))bis(1,3-naphthalenedisulfonic acid);

7,7'-(carbonyl-bis(imino-N-methyl-4,2-pyrrolecarbonylimino(N-methyl-4,2-pyrrolecarbonylimino(N-methyl-4,2-pyrrole)carbonylimino))bis(1,3-naphthalenedisulfonicacid);

7,7'-(carbonyl-bis(imino-N-methyl-4,2-pyrrolecarbonylimino(N-methyl-4,2-pyrrole)carbonylimino))bis(2,4,6-naphthalenetrisulfonic acid);

7,7'-(carbonyl-bis(imino-N-methyl-4,2-pyrrolecarbonylimino(N-methyl-4,2-pyrrole)carbonylimino))bis(2,3,5-naphthalenetrisulfonic acid); and pharmaceutically acceptable equivalents.

7. The method of claim 6, wherein the compound of formula I is selected from the group consisting of:

suramin;

8,8'-[carbonylbis(imino-3,1-phenylene)]bis-(1,3,5-naphthalenetrisulfonic acid);

5-[[[1-methyl-4-[[[[1-methyl-6-[[(4,5,7-trisulfo-1-naphthalenyl)amino]carbonyl]-1H-pyrrol-3-yl]amino]carbonyl]amino]-1H-pyrrol-2-yl]carbonyl]amino]-1,3,8-naphthalenetrisulfonic acid;

4-[[[1-methyl-4-[[[[1-methyl-5- [[(4-sulfo-1 naphthalenyl)amino]carbonyl]-1H-pyrrol-3-yl]amino]carbonyl]amino]-1H-pyrrol-2-yl]carbonyl]amino]-1-naphthalenesulfonic acid; and pharmaceutically acceptable equivalents.

8. The method of claim 1, wherein:

m and n are each 0;

Y is —R$_2$; and

R$_1$ is a naphthyl group substituted with 1, 2 or 3 sulfonic acid group(s).

9. A method for treating a glutamate abnormality in a mammal, comprising administering to said mammal an effective amount of a compound of formula I

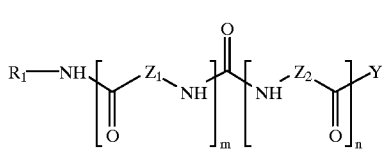

I or a pharmaceutically acceptable equivalent, wherein:

m and n are independently 0, 1, 2 or 3;

Y is —R$_2$ or —NHR$_2$;

R$_1$ and R$_2$ are independently an aryl or heteroaryl group substituted with one or more substituent(s);

Z$_1$ and Z$_2$ are independently a moiety of formula II, III or IV

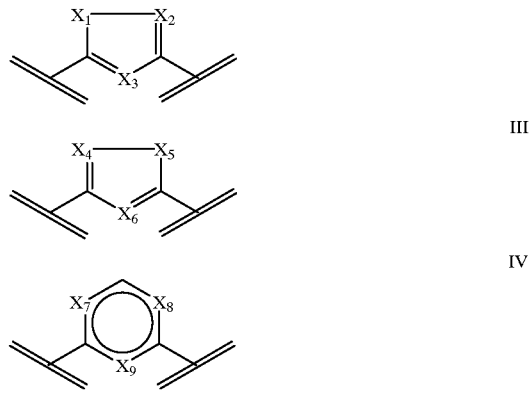

X$_1$ and X$_5$ are independently CHR$_3$ or NR$_3$;

X$_2$, X$_3$, X$_4$, X$_6$, X$_7$, X$_8$ and X$_9$ are independently CR$_3$ or N; and R$_3$ is H or CH$_3$;

provided that when m and n are independently 1, 2 or 3, Y is —NHR$_2$, R$_2$ is naphthyl substituted with 1, 2 or 3 sulfonic acid(s), Z$_1$ and Z$_2$ are each a moiety of formula II, X$_1$ and X$_2$ are each CH, X$_3$ is NR$_3$, and R$_3$ is CH$_3$, then the glutamate abnormality is not a demyelinating disease; and when the compound of formula I is suramin, then the glutamate abnormality is not a CNS neurodegenerative disorder or a demyelinating disease.

10. The method of claim 9, wherein the glutamate abnormality is selected from the group consisting of compulsive disorder, stroke, demyelinating disease, schizophrenia, Parkinson's disease, ALS, diabetic neuropathy, pain, anxiety, anxiety disorder and memory impairment.

11. The method of claim 10, wherein the glutamate abnormality is diabetic neuropathy.

12. The method of claim 10, wherein the glutamate abnormality is schizophrenia.

13. The method of claim 10, wherein the glutamate abnormality is pain.

14. The method of claim 13, wherein the compound of formula I is administered in combination with an effective amount of morphine.

15. A method for effecting a neuronal activity in a mammal, comprising administering to said mammal an effective amount of a compound of formula I

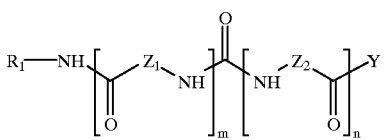

I or a pharmaceutically acceptable equivalent, wherein:

m and n are independently 0, 1, 2 or 3;

Y is —R$_2$ or —NHR$_2$;

R$_1$ and R$_2$ are independently an aryl or heteroaryl group substituted with one or more substituent(s);

Z$_1$ and Z$_2$ are independently a moiety of formula II, III or IV

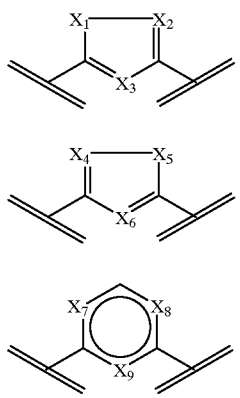

II

III

IV

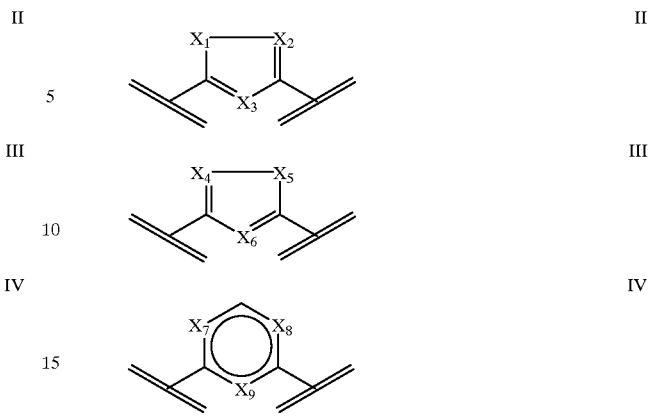

II

III

IV $X_1$ and $X_5$ are independently $CHR_3$ or $NR_3$;

$X_2$, $X_3$, $X_4$, $X_6$, $X_8$ and $X_9$ are independently $CR_3$ or N; and $R_3$ is H or $CH_3$;

provided that when m and n are independently 1, 2 or 3, Y is —$NHR_2$, $R_2$ is naphthyl substituted with 1, 2 or 3 sulfonic acid(s), $Z_1$ and $Z_2$ are each a moiety of formula II, $X_1$ and $X_2$ are each CH, $X_3$ is $NR_3$, and $R_3$ is $CH_3$, then the effecting a neuronal activity is not treating a demyelinating disease; and when the compound of formula I is suramin, then the effecting a neuronal activity is not treating a CNS neurodegenerative disorder or a demyelinating disease.

16. The method of claim 15, wherein the neuronal activity is selected from the group consisting of stimulation of damaged neurons, promotion of neuronal regeneration, prevention of neurodegeneration and treatment of a neurological disorder.

17. The method of claim 16, wherein the neurological disorder is selected from the group consisting of peripheral neuropathy caused by physical injury or disease state, traumatic brain injury, physical damage to spinal cord, stroke associated with brain damage, demyelinating disease and neurological disorder relating to neurodegeneration.

18. The method of claim 17, wherein the neurological disorder relating to neurodegeneration is selected from the group consisting of Parkinson's disease and ALS.

19. A method for treating a prostate disease in a mammal, comprising administering to said mammal an effective amount of a compound of formula I

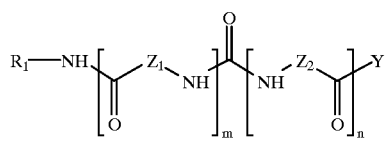

I or a pharmaceutically acceptable equivalent, wherein:

m and n are independently 0, 1, 2 or 3;

Y is —$R_2$ or —$NHR_2$;

$R_1$ and $R_2$ are independently an aryl or heteroaryl group substituted with one or more substituent(s);

$Z_1$ and $Z_2$ are independently a moiety of formula II, III or IV $X_1$ and $X_5$ are independently $CHR_3$ or $NR_3$;

$X_2$, $X_3$, $X_4$, $X_6$, $X_7$, $X_8$ and $X_9$ are independently $CR_3$ or N; and $R_3$ is H or $CH_3$;

provided that when the compound of formula I is suramin, then the prostate disease is not prostate cancer.

20. The method of claim 19, wherein the prostate disease is prostate cancer.

21. A method for treating cancer in a mammal, comprising administering to said mammal an effective amount of a compound of formula I

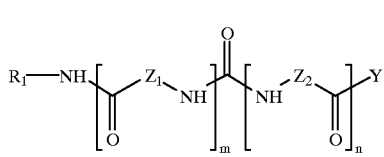

I or a pharmaceutically acceptable equivalent, wherein:

m and n are independently 0, 1, 2 or 3;

Y is —$R_2$ or —$NHR_2$;

$R_1$ and $R_2$ are independently an aryl or heteroaryl group substituted with one or more substituent(s);

$Z_1$ and $Z_2$ are independently a moiety of formula II, III or IV

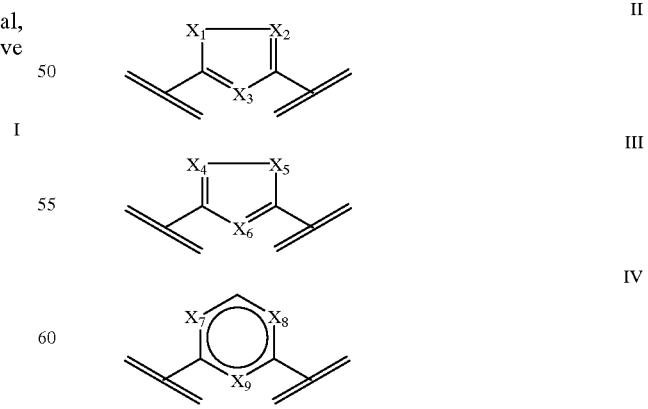

II

III

IV $X_1$ and $X_5$ are independently $CHR_3$ or $NR_3$;

$X_2$, $X_3$, $X_4$, $X_6$, $X_7$, $X_8$ and $X_9$ are independently $CR_3$ or N; and $R_3$ is H or $CH_3$;

provided that when the compound of formula I is suramin, then the cancer is not prostate cancer.

22. A method for inhibiting angiogenesis in a mammal, comprising administering to said mammal an effective amount of a compound of formula I

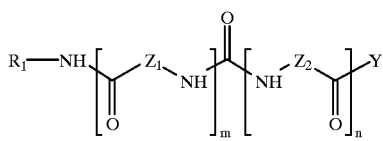

I or a pharmaceutically acceptable equivalent, wherein:

m and n are independently 0, 1, 2 or 3;

Y is —$R_2$ or —$NHR_2$;

$R_1$ and $R_2$ are independently an aryl or heteroaryl group substituted with one or more substituent(s);

$Z_1$ and $Z_2$ are independently a moiety of formula II, III or IV

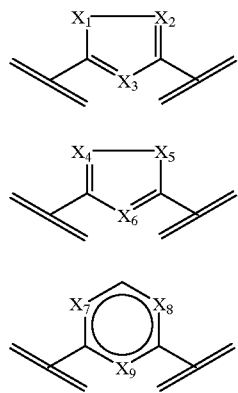

II

III

IV $X_1$ and $X_5$ are independently $CHR_3$ or $NR_3$;

$X_2$, $X_3$, $X_4$, $X_6$, $X_7$, $X_8$ and $X_9$ are independently $CR_3$ or N; and $R_3$ is H or $CH_3$.

23. A pharmaceutical composition comprising:

(i) an effective amount of a compound of formula I for inhibiting NAALADase enzyme activity or angiogenesis, in a mammal in need thereof effecting a neuronal activity, or treating a glutamate abnormality, prostate disease or cancer

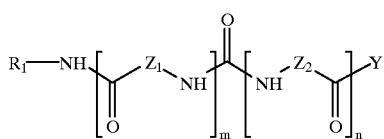

I or a pharmaceutically acceptable equivalent, wherein:

m and n are independently 0, 1, 2 or 3;

Y is —$R_2$ or —$NHR_2$;

$R_1$ and $R_2$ are independently an aryl or heteroaryl group substituted with one or more substituent(s);

$Z_1$ and $Z_2$ are independently a moiety of formula II, III or IV

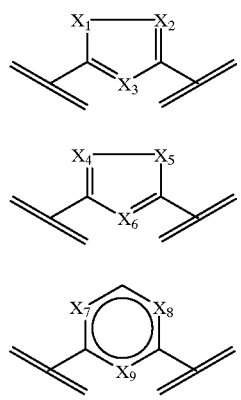

II

III

IV $X_1$ and $X_5$ are independently $CHR_3$ or $NR_3$;

$X_2$, $X_3$, $X_4$, $X_6$, $X_7$, $X_8$ and $X_9$ are independently $CR_3$ or N; and $R_3$ is H or $CH_3$;

provided that when m and n are independently 1, 2 or 3, Y is —$NHR_2$, $Z_1$ and $Z_2$ are each a moiety of formula II, $X_1$ and $X_2$ are each CH, $X_3$ is $NR_3$, and $R_3$ is $CH_3$, then $R_2$ is not naphthyl substituted with 1, 2 or 3 sulfonic acid(s); and provided that the compound of formula I is not suramin; and (ii) a pharmaceutically acceptable carrier.

* * * * *